(12) United States Patent
Luria (10) Patent No.: US 8,552,135 B2
(45) Date of Patent: Oct. 8, 2013

(54) SUBSTITUTED POLYALKOXYSILOXANE COMPOSITIONS AND METHODS OF USE

(75) Inventor: Leonard William Luria, Tampa, FL (US)

(73) Assignee: One Unlimited, Inc., Tampa, FL (US)

( * ) Notice: Subject to any disclaimer, the term of this patent is extended or adjusted under 35 U.S.C. 154(b) by 0 days.

(21) Appl. No.: 13/446,064

(22) Filed: Apr. 13, 2012

(65) Prior Publication Data

US 2012/0196832 A1    Aug. 2, 2012

Related U.S. Application Data

(63) Continuation-in-part of application No. 12/701,312, filed on Feb. 5, 2010, now Pat. No. 8,158,740, which is a continuation-in-part of application No. 11/542,996, filed on Oct. 4, 2006, now Pat. No. 7,687,592.

(51) Int. Cl.
*C08G 77/18* (2006.01)
*A61K 31/80* (2006.01)

(52) U.S. Cl.
USPC .... 528/29; 424/78.06; 424/78.08; 424/78.09; 428/429; 428/450

(58) Field of Classification Search
None
See application file for complete search history.

(56) References Cited

U.S. PATENT DOCUMENTS

| | | | |
|---|---|---|---|
| 3,133,111 A | 5/1964 | Wheeler et al. | |
| 3,600,418 A | 8/1971 | Bailey et al. | |
| 4,172,186 A | 10/1979 | Scott et al. | |
| 4,431,789 A | 2/1984 | Okazaki et al. | |
| 4,487,809 A | 12/1984 | Koerner et al. | |
| 5,073,195 A | 12/1991 | Cuthbert | |
| 5,144,054 A | 9/1992 | Shioya et al. | |
| 5,208,360 A | 5/1993 | Ward et al. | |
| 5,871,558 A | 2/1999 | Takei | |
| 6,251,981 B1 | 6/2001 | Tanaka et al. | |
| 6,258,969 B1 | 7/2001 | Sawai et al. | |
| 6,790,451 B2 | 9/2004 | Nakanishi | |
| 7,687,592 B2 | 3/2010 | Runnels et al. | |
| 8,158,740 B2 * | 4/2012 | Luria | 528/29 |
| 2004/0146472 A1 | 7/2004 | Nakanishi | |
| 2004/0236003 A1 | 11/2004 | Del Torto et al. | |
| 2005/0033002 A1 | 2/2005 | Kishan | |
| 2005/0186360 A1 * | 8/2005 | Oya et al. | 428/1.1 |
| 2005/0202257 A1 | 9/2005 | Gerritsen et al. | |
| 2006/0156941 A1 * | 7/2006 | Mori et al. | 101/467 |
| 2007/0049716 A1 | 3/2007 | Sayre | |

FOREIGN PATENT DOCUMENTS

| | | |
|---|---|---|
| GB | 875 109 | 8/1961 |
| JP | 31-007874 | 9/1956 |
| JP | 02-256687 | 10/1990 |
| JP | 2001-172389 | 6/2001 |
| JP | 2004-176050 | 6/2004 |
| JP | 2006-307115 | 11/2006 |
| WO | WO 98/36016 | 8/1998 |

OTHER PUBLICATIONS

Jayakannan, M. et al. "Preparation of polyethers via proton acid catalyzed transetherification reactions" *Macromolecular Chemistry and Physics*, 2000, pp. 759-767, vol. 201, No. 7.

Pratt, E.F. et al. "Reaction Rates by Distillation, The Etherification of Phenylcarbinols" Department of Chemistry, *University of Maryland*, 1949, pp. 2846-2849, vol. 71.

Cao, S. et al. "Antimicrobial activity and mechanism of action of Nu-3, a protonated modified nucleotide" *Annals of Clinical Microbiology and Antimicrobials*, 2011, pp. 1-9, vol. 10, No. 1.

* cited by examiner

*Primary Examiner* — Marc Zimmer
(74) *Attorney, Agent, or Firm* — Saliwanchik, Lloyd & Eisenschenk (57) ABSTRACT

Linear polydialkoxysiloxanes with 2-8 polymeric units have been reacted with alcohols by a transetherification reaction to provide hydrophilic and water soluble silicone products. The glycerol substituted siloxanes in particular are effective in topically treating skin lesions such as radiation burns. Compositions including the substituted polydialkoxysiloxane products inhibit biofilm formation when used as coatings on hard surfaces.

20 Claims, 2 Drawing Sheets

SUBSTITUTED POLYALKOXYSILOXANE COMPOSITIONS AND METHODS OF USE

This is a continuation-in-part of U.S. patent application Ser. No. 12/701,312, filed Feb. 5, 2010, now U.S. Pat. No. 8,158,740, which is a continuation-in-part of U.S. patent application Ser. No. 11/542,996, filed Oct. 4, 2006, now U.S. Pat. No. 7,687,592, the disclosures of which are hereby incorporated by reference in their entirety, including all figures, tables and amino acid or nucleic acid sequences.

BACKGROUND OF THE INVENTION

1. Field of the Invention

The invention relates to the preparation and use of modified polydialkoxysiloxanes as protective barriers and as treatments for skin damage.

2. Description of Background Art

Silicone fluids having remarkable versatility and new uses are continually being developed and sought. The name "silicone" denotes a polymer with the formula shown in I:

$$\frac{(R_n SiO_4 - n)_m}{2} \qquad \text{I}$$

where n is between 0 and 3, m is 2 or larger and R is typically alkyl. The term "silicone" arose from the work of early investigators who erroneously assumed that oxygen was bound to silicone by a double bond similar to that in ketones.

The simplest silicones are polydimethyl siloxanes having the structure:

$$CH_3-Si-O[-Si-O]_n-Si-CH_3 \qquad \text{II}$$

The repeating unit of the polymer, [—Si—O—], the dimethylsiloxane unit, in the dimethoxysiloxane unit shown in II above is referred to as the D unit so that the structure above is often referred to as $MD_nM$. Structure II is shown as linear, although silicones can have branched points referred to as T and Q groups. Branch points form a network and introduce rigidity into the structure.

The methyl group in I can be substituted by other groups, most commonly phenyl, vinyl and hydrogen. The substitutions, branching and molecular weight of the silicone polymers determine properties and use.

Low molecular weight siloxanes are used as monomers and terminators in the polymerization of higher molecular weight silicones.

In order to provide water soluble silicones, several methods to chemically modify the silicone structure in order to circumvent the need for emulsification have been tested. Some commercially available compounds include dimethicone polyols (SILTECH), cyclomethicones (CLEARDO) and polyesters (ZENITECH).

Liquid silicone polymers, such as polydimethoxysiloxane and polydiethoxysiloxane, have a very low solubility in water or aqueous solutions. In order to accommodate this property, slightly soluble siloxane compounds can be emulsified with surfactants to form aqueous emulsions, which are stable for long periods up to several months. Such emulsions consist of a suspension of very small droplets of liquid silicone that may be visible microscopically, but are more easily characterized and monitored by light scattering. Despite the inherent instability of most emulsions, many cosmetic products have been successfully based on emulsification. Extensive experimentation in selecting the optimal surfactant and in confirming the emulsion stability of the product over an appropriate time period is usually necessary.

Efforts have also been made to develop hydrophobic silicones; for example, a reaction between alcohols and alkoxysiloxanes is typically used to introduce hydrophobic properties. Wood contains hydroxyl groups and, in the form of a finely divided flour, has been reacted with oligoethoxysiloxanes to produce a solid material with low water affinity and compatibility with hydrocarbon polymers.

Personal care products rely heavily on the use of silicones with at least half of the U.S. market for silicones used in antiperspirants and deodorants. Cosmetics traditionally use formulations that include octamethylcyclotetrasiloxane, also known as D4, in topical skin creams because of its lack of toxicity and low cost. A related compound, D5 or decamethylcyclopentasiloxane has to some extent replaced use of D4, which recently has raised concerns related to bioaccumulation, particularly in marine environments. Despite these concerns, the general consensus among manufacturers and suppliers appears to be that the cyclic silicones are safe. In a recent study, the Canadian government determined that siloxane D5 is safe for use in personal care products such as topical skin creams, antiperspirants and hair products. These siloxanes are used in amounts varying from 0.01% in skin cleansers to up to 0.65% in hair conditioners and hair grooming products. The market in 2009 for cyclic methyl siloxanes was 104 million pounds (Chem & Engineering News, vol. 89, No. 18, May 2, 2011).

SUMMARY OF THE INVENTION

The invention concerns the use of linear polyalkoxy siloxanes which have been chemically modified by a transetherification reaction with alcohols to produce polymeric silicon products with hydrophilic side groups on a silicone backbone. The starting material is a linear dialkoxy siloxane typically having 2-15 polymer units. Polydiethoxy or polydimethoxy silicones are reacted with a primary or secondary alcohol through a transetherification exchange. Compositions comprising silicone products with hydrophilic substitutions show surprising therapeutic effectiveness in treatment of burns, skin infections and disease produced lesions. Reaction of diethoxy or dimethoxy polysiloxanes with alcohols using the described transetherification reaction produces novel polysiloxane compositions which can be customized for specific applications.

The reaction with alkoxy groups requires a free alcohol group. The reaction is reversible and in a closed system would reach equilibrium with all species present at concentrations not significantly different from each other. When methoxy and ethoxy silicones are substituted with alcohols having larger or hindered groups the equilibrium may be forced to completion by removing methanol or ethanol as the more volatile products.

The reaction may be carried out on a practical scale by mixing a polydialkoxysiloxane with the alcohol to be coupled and heating to about 200° F. for 20 hr or more. After cooling to room temperature, a water soluble portion can be obtained by mixing with water and recovering water soluble product by centrifugation, decantation or filtration. The product is a heterogeneous composition of predominately linear substituted polydialkoxysiloxane polymers. The polymers have 8-15 units and are substituted with the alcohol to varying degrees along the silicone backbone. The number of polymer units will depend on the starting material which is usually a dialkoxy siloxane with 8-15 polymer units. If separation of the products is desired, they can be fractionated by high performance liquid chromatography (HPLC) or used without fractionation in cosmetic or therapeutic preparations. The major products appear to result from replacement of about 30-70% of the alkoxy groups on the siloxane backbone with a selected alcohol.

Silicones substituted with glycerol or BRONOPOL or combinations of the two are typically at least 5% water soluble and when applied in aqueous solution to the skin leave a very thin adherent coating. The film is nonwettable and provides an exceptionally smooth texture which is retained through repeated exposures to water. The water solubility of such modified silicones might suggest that topical preparations applied to skin are readily removed by washing but surprisingly it appears that hydrophobic interactions between the polysiloxane and the skin impart strong adherence.

In an important aspect, the invention focuses on "hydrophilic silicones," i.e., linear polydialkoxysiloxanes substituted with hydrophilic groups selected to impart hydrophilic properties. The degree of substitution and the alcohol substituent determine the degree of hydrophilicity. Compositions for a designated use can be produced by modification of the production process. The amount of transetherification product in the polydialkoxysiloxane compositions determines properties for targeted products, including topical skin preparations, waxes, sealants, elastomers and a variety of personal care products. These modified silicones when used in cosmetics, require no emulsification and are stable in solution for long periods of time.

In one application of the invention, a glycerol substituted polydiethoxy siloxane composition was found to be an effective inhibitor of biofilm formation when applied in low concentrations to hard surfaces such as glass. The compound appears to form a monomolecular coating on the surface which inhibits biofilm formation of algae and to a lesser extent prevents biofilm from bacterial species such as *Pseudomonas* and *Staphylococcus. aureus*.

Alcohols with different properties can be reacted with polydialkoxysiloxanes; for example, BRONOPOL substituents provide a compound with antibacterial properties. One product from transetherification with BRONOPOL is initially obtained as a liquid which crystallizes to a stable water soluble solid. This is advantageous because solid forms can be shipped in dry form and prepared in solution prior to use.

The described silicone products can also be used as additions to finishes for many manufactured products since such additions discourage the accumulation of dust or other airborne contaminants. They are also potentially useful as a special class of lubricants when attached covalently to surfaces using the reactions described, provided that the surface to be treated has free alcoholic hydroxyl groups to act as an anchor for the substituted polydialkoxysiloxanes.

The hydrophilic silicone products with glyceryl substituents are also contemplated as useful for coating stents and implants where prevention of biofilm is required. In some medical applications, use in inhalation therapies may be appropriate. The compositions have already been shown to promote skin healing and regeneration when topically administered to areas in the ear canal in treatment of chronically draining ear.

A particularly important medical treatment application is the healing effect of some of the hydrophilic substituted polydialkoxysiloxanes on radiation burn injuries. Skin irritation and burning is common in cases where patients undergo radiation treatment associated with certain cancers. Topical application of glycerol substituted polydialkoxysilane compositions relieves pain and accelerates healing compared to treatment with commonly used burn or cortisone ointments. The glycerol polysiloxanes can be used in combination with topical antibacterials; for example, when applied with Nu-3 (butyl-phosphate-5'-thymidine-3'-phosphate), to treat burn wound infections from *Pseudomonas aeruginosa*, there was only a slight decrease in antibacterial effectiveness of Nu-3. Nubiotics are a new class of antibiotic agents with broad spectrum activity.

DEFINITIONS AND TERMS

The polydialkoxysiloxanes used as starting materials for preparing compositions containing alcohol substituents are short polymers, generally having 2-15 linear —Si—O—Si— units with OR (alkoxy) groups attached as side chains on the silicone backbone. Some of the products are produced from polydialkoxysiloxanes with 2-8 polymer units. The products are produced by a transetherification reaction with alkoxy groups such as methoxy or ethoxy, and which have varying degrees of replacement of the alkoxy groups. The products are linear $[Si(OR)_2—O—]_n$ where R is either the original methoxy or ethoxy group or the alcohol replacing one or more of the alkoxy groups. Any reference to polysiloxane or polydialkoxysiloxane refers to the linear form of the silicon polymers as described.

The name polydiethoxysiloxane is also referenced in the literature as ethyl polysilicate. All references herein to a polydialkoxysiloxane refer to the linear polymer substituted along the silicone backbone by the alkoxy groups and groups replacing the starting material alkoxy pendant groups at the silicon. The reactions with alcohols result in substitution of the alkoxy group, replacing some or all of the alkoxy groups. The compositions described herein are mixtures of polysiloxanes with typically 30-70% alkoxy group substitution and 2-8 polymeric units. Higher degrees of substitution can be reached by using longer reaction times and higher temperatures; however, at temperatures over 130° C. (266° F.) the products tend to include branched polymers in addition to linear substituted polyalkoxysiloxanes. The optimum substitutions for retaining linearity appear to be in the 50-60% range, with substitutions likely at alternating positions along the silicone backbone.

BRIEF DESCRIPTION OF THE FIGURES

FIG. 1 is a graph showing summary of data from a study on military personnel from a group training for deployment. The training period was 2 weeks in a severe environment of wind, sun and extreme temperatures with skin conditions resulting from chaffing, blisters, sunburn, wind burn, folliculitis, razor burn and insect bites. All individuals carried 70 pound back packs under extremely demanding physical conditions. Of 40 respondents, 34 used the test products and provided feedback.

DETAILED DESCRIPTION OF THE INVENTION

The invention relates to new silicone compositions which are unusually effective as barrier materials and as therapeutic adjuncts for treatment of burns, cold sores and a variety of skin irritations, including topical and radiation dermatitis, acne and actinic skin damage The disclosed compositions comprise predominately linear polydialkoxysiloxanes with glyceryl groups substituted for some of the alkoxy groups along the backbone. The products are suitable for cosmetic or barrier products that are water or oil based. When topically applied in a thin coating to surfaces such as skin, the material withstands numerous washings with detergents and water.

The inventive compositions can also be used in low concentrations in cosmetics intended for topical use at concentrations of 0.01% up to 1%. In suitable cosmetically approved formulations, they can be blended into lotions and creams at concentrations up to 20% without destroying the emulsions; and preferably 1%-5% for standard products or at higher concentrations up to 20% for barrier products. The glycerol substituted diethoxy or dimethoxy polysiloxanes can be emulsified with lotions or creams at concentrations up to 20% without destabilization.

Carriers useful in formulating the compositions for particular use may be based on an aqueous gel, anhydrous gel, a water-in-oil emulsion, an oil-in-water emulsion, or water. Examples include purified water, triethanol amine, phenoxyethanol, benzene free carbomer, methylparaben, isopropylparaben, ispropylparaben and butylparaben.

Some compositions will preferably include an emollient, a neutralizer thickener, and/or a preservative. Preservatives are usually added in order to increase shelf life and are used in numerous cosmetic preparations intended for use over a period of time and which tend to be stored at or above room temperature. Neutralizers may be used to adjust pH, which for skin preparations is preferably on the acidic side below pH 7, often in the range of pH 3.5-4.0. Thickeners, also well known in the art, may be added for texture and convenience in application.

Emollients are often included in cosmetic preparations to enhance penetration of active ingredients. Organic acids are particularly desirable for use in the disclosed formulations because they act not only as emollients but are also good exfoliators.

There are a number of other agents that can be combined with the disclosed compositions, including vitamins and sunscreens. Vitamins found in many commercial face creams include vitamins A, E, C, D, F, $CoQ_{10}$. These may be added alone or in combination for possible anti-oxidative benefits.

Sunscreen agents include p-aminobenzoic acid (PABA), paraben, digalloyl trioleate, dioxybenzone, ethyldihydroxy propyl PABA, ethylhexyl p-methoxycinnamate, ethylhexyl salicylate, glyceryl PABA, homosalate, menthyl anthranilate, octocrylene, octyl methoxycinnamate, octyl salicylate, oxybenzone, octyl dimethyl PABA, red petrolatum, titanium dioxide and zinc oxide. These additional ingredients are often used in skin preparations to protect against UV exposure; however, care must be used in the selection as not all protect against UVA and some may cause skin irritation.

Therapeutic applications when used topically may require different considerations in formulation such as whether or not combined with active pharmaceutical agents, sensitivity and absorption characteristics.

Pharmaceutical compositions containing one or more of the compositions produced by any of the described transetherification reactions are preferably administered topically. In all cases the form must be sterile and stable under the conditions of manufacture and storage and must be preserved against the contaminating action of microorganisms, such as bacteria and fungi. The carrier can be a solvent or dispersion medium containing, for example, water, ethanol, a polyol such as glycerol, propylene glycol, liquid polyethylene glycol, and the like, including suitable mixtures thereof, and vegetable oils. The proper fluidity can be maintained by the use of a coating such as lecithin, by the maintenance of the required particle size for dispersions and by the use of surfactants. The prevention of the action of microorganisms can be effected by various antibacterial and antifungal agents such as parabens, chlorobutanol, phenol, sorbic acid, thimerosal and the like. In many cases, isotonic agents may be included, for example, sugars or sodium chloride.

The compositions of the present invention will typically be used topically; however, in limited circumstances one may need to administer certain preparation into the body. Sterile injectable solutions are prepared by incorporating the active compounds comprising the compositions in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that a water soluble compound as an active ingredient is well understood in the art. Such compositions can be prepared as a suspension or dispersion. Solid products can be isolated from the reaction of polydiethoxysiloxanes with some alcohols. Mixed glyceryl BRONOPOL substitutions are water soluble and can be prepared as pharmaceutically acceptable solutions by dissolving in water. The preparation can also be emulsified.

Upon formulation, solutions or solid forms will be administered in a manner compatible with the dosage formulation and in such amount as is therapeutically effective. Such determinations are routinely determined by those skilled in the art, by testing for toxicity ($LD_{50}$ for example) and amounts sufficient to produce a therapeutic effect. The formulations can be administered in a variety of dosage forms.

Modification of silicones in accordance with the invention produces materials that are suitable as the basis for numerous dermatological preparations, both human and veterinary. In addition, possible uses may be found as materials for construction, paints and coatings for home, agricultural and industrial products where some affinity for water is desirable.

The inventive material is both water soluble and compatible with human skin, where it is able to form an extremely thin film. This film resists washing with water and imparts a feeling of softness, while protecting the skin from bacterial and fungal invasion by virtue of added protective agents.

Polysiloxanes substituted with glycerol or BRONOPOL, or combinations of the two, can be quite water soluble and, when applied in aqueous solution to the skin, leave a very thin film on the skin. They also can impart hydrophobicity and an exceptionally smooth texture, which remains despite repeated exposures to water. The water solubility of such modified silicones indicates that hydrophobic interactions between the polysiloxane and the skin are taking place. The modified silicones of the invention have been shown to promote healing in burn cases, both in terms of accelerating the healing process and in moderating pain.

A method of preparing water soluble silicones is provided. The method comprises the reaction between a linear polydialkoxysiloxane (the alkoxy usually being either methoxy or ethoxy) and an alcohol. Examples of alcohols include glycerol, BRONOPOL, and numerous other alcohols as well as mixtures of these alcohols as shown in Table 1.

TABLE 1

| Primary Alcohols | Secondary Alcohols | Other alcohol |
| --- | --- | --- |
| 1-propanol | 1,2-propanediol | Glycerol |
| 2-propanol | 1,3-propanediol | BRONOPOL |
| 1-butanol | 1,6-hexanediol | |
| 1-pentanol | | |
| 1-hexanol | | |

In the inventive process, the alkoxy group $OR_1$, typically methoxy or ethoxy, of the siloxane undergoes a reaction with the hydroxyl group of an alcohol, $R_2OH$, to replace the alkoxy group with the alcohol as shown in Equation 1.

To carry out this reaction, a polydialkoxysiloxane is mixed with an alcohol, preferably without the addition of a catalyst. Progress of the reaction is monitored by sampling the reaction mixture and testing for the appearance of water-soluble material. Reaction velocity may be increased by heating the reaction mixture. When a satisfactory amount of water-soluble material has been produced and recovered, the catalyst, if any, is removed or neutralized. The water-soluble fraction of the reaction mixture can be used directly, usually in a 5% by volume aqueous solution or further purified into active components, using chromatography or other means well known in the art of separation technology.

In general, it has been discovered that certain alcohols react under mild conditions with alkoxy groups situated on a linear polysiloxane chain. The alkoxy groups undergo an "exchange reaction" or a "transetherification"; for example, the methoxy or ethoxy groups of the polyalkoxysiloxane are lost as methanol or ethanol while the alkoxy moiety of the reacting alcohol (usually of higher boiling point than that of methanol or ethanol) is bound to the silicon of the polysiloxane backbone. The reaction thus provides a simple and rapid methodology for the modification of the chemical and physical properties of "silicones" containing alkoxy groups thereby providing new chemical structures suitable for numerous applications.

The reaction with alkoxy groups requires a free alcohol group which is typically a primary, aliphatic group. It is expected that reaction will occur also with secondary or tertiary groups, or with phenols, but may proceed with greatly decreased rates, particularly where some steric hindrance arises due to the structure of the alcohol.

In theory, the above reaction is probably readily reversed so that, in a closed system, equilibrium is likely reached when all the species indicated are present at concentrations not drastically different from each other. However, when the reactive groups on the silicone are methoxy or ethoxy, while glycerol is somewhat larger, the above reaction will easily go to completion by allowing the more volatile alcohol product to escape. In the present invention, two alcohols, glycerol and BRONOPOL are shown as exemplary, but other alcohols can be used for the inventive reactions without departing from the scope of the invention. Equation 2 illustrates the reaction between a polydimethoxysiloxane and glycerol:

The reaction is carried out on a practical scale by mixing an alkoxypolysiloxane, preferably methoxy or ethoxy, with the alcohol to be coupled to the siloxane and heating between about 140°-300° F. The reaction is run under dry conditions and preferably under reduced pressure. Moisture should be excluded to prevent hydrolysis which significantly reduces yield of product.

The reaction can be driven to completion by removing volatile reaction products for example, methanol or ethanol when the starting material is dimethoxy or diethoxy polysiloxane. Increasing the temperature is a convenient method to speed the reaction so that efficiency of removal of the alcohol during the reaction will influence reaction time. The more efficient the removal of the alcohol, the less the time period is for the reaction to reach maximum equilibrium.

More particularly, at a lower temperature range of between about 140° F. and 190° F., the heating period that is necessary for the reaction to go to completion (to reach maximum equilibrium) is greater than 20 hours, and can in fact last up to several days. At between about 195° F. and 205° F., reaction time (to reach maximum equilibrium) is between about 20 and 22 hours. By increasing the temperature to between about 210° F. and 220° F., reaction time (to reach maximum equilibrium) is reduced to between about 12 and 18 hours. At an even higher temperature of between about 225° F. and 235° F., the reaction time (to go to completion—to reach maximum equilibrium) is dramatically reduced to between about 5 and 8 hours. This significant time savings will allow the manufacturing process to be contained within a single 8 hour shift, thereby reducing the overall cost of the process, and eliminating additional variables that could affect the resulting end product. When the temperature is increased to greater than 250° F., reaction time is decreased even further; however, the quality of the reaction and therefore the end product will be impacted. Mass-Spectrometry has confirmed that the alcohol reacts with the siloxanes in all instances.

The addition of an acidic catalyst, such as hydrochloric acid or trichloroacetic acid, or a basic catalyst, such as N-ethyldisopropylamine or triethylamine, to the reaction may be useful in achieving desired reaction rates. If the substituting alcohol has, in addition to the hydroxyl group consumed in the coupling reaction, additional hydrophilic groups, the polysiloxane product may be water soluble.

After heating the reaction mixture for the specified time and then cooling to room temperature, water soluble products can be extracted. Any solid material can be separated by centrifugation, decantation or filtration. The residue left after the extraction with water contains polysiloxane species that have reacted with a number of alcohol molecules too few to give water solubility but, nevertheless, with a sufficient number to become very hydrophilic. Such material is suitable for incorporation into dermatological salves and creams or other products where some wettability is desirable.

The water soluble material produced by this process can be fractionated, either by size exclusion chromatography (SEC) or high performance liquid chromatography (HPLC). Fractionation by HPLC can serve to separate reaction products into many categories with slightly varying properties. This results from the high number of ways in which the linear polysiloxane backbone structure may be substituted, both with respect to the degree of substitution and with respect to the arrangement of substituent groups along the polysiloxane chain.

Examples of the synthesis of hydrophilic silicones by reacting polyalkoxysiloxones with aliphatic alcohols are given in Tables 2-4 below along with a brief indication of some of the properties of these products:

TABLE 2

| Example | Silicone substituents | Amt Silicone | Amt Glycerol | Amt BRONOPOL | Hrs. @ 200° F. | Result |
|---|---|---|---|---|---|---|
| 214-112-7 | —OMe | 5 ml | 2 ml | 3 g | 20 | Transparent gel indicating extensive reaction. |
| 214-112-8 | —OEt | 5 ml | 2 ml | 3 g | 20 | Very little reaction as judged visually. Small amt. gel; most liquid silicone left. |
| 214-113-8 | —OEt | 5 ml | 2 ml | 3 g | 60 | Extensive reaction. Stiff transparent gel. Skin test: judged better than Example 214-112-7 |
| 214-116-9 | —OMe | 5 ml | 0.5 ml | 0.5 g | 20 | Clear colorless liquid; 2 mm solid gel on bottom of vial. Added 15 ml $H_2O$ & mixed → turbid susp. Little foaming; 8da later → gel. |
| 214-116-10 | —OEt | 5 ml | 0.5 ml | 0.5 g | 20 | Clear slightly amber liquid with foaming; transparent solid on bottom. Added 15 ml $H_2O$ & mixed up → turbid suspension (much foaming). 8 days later: had formed clear liquid—no gel. |

TABLE 3

| Example | Silicone substituents | Amt Silicone | Amt Glycerol | Amt BRONOPOL | Hrs. @ 200° F. | Result |
|---|---|---|---|---|---|---|
| 214-116-11 | —OMe | 5 ml | 0.2 ml | 0.1 g | 20 | Clear colorless liquid with solid transparent layer on bottom. 15 ml $H_2O$ added & mixed— turbid suspension → no foam. 8 days later: had formed stiff gel throughout. |

TABLE 3-continued

| Example | Silicone substituents | Amt Silicone | Amt Glycerol | Amt BRONOPOL | Hrs. @ 200° F. | Result |
|---|---|---|---|---|---|---|
| 214-116-12 | —OEt | 5 ml | 0.2 ml | 0.1 g | 20 | Clear, pale amber liquid with small translucent deposit on bottom. 15 ml $H_2O$ added & shaken → foam. 8 days later: clear liquid, no gel. |
| 214-133-Sup. 1 | —OEt | 20 ml | 0 | 2.0 g | 20 | $H_2O$ extraction→ 75 m; ext., 3.8 g dry wt. Excellent cosmetic appeal. |

TABLE 4

| Example | Silicone substituents | Amt Silicone | Amt Glycerol | Amt BRONOPOL | Hrs.@ x° F. | Result |
|---|---|---|---|---|---|---|
| 215-281 | —OEt | 64.25 g | 38.5 g | | 20 Hr 200° F. | 2 layers—lower layer water soluble clear liquid—upper layer viscous liquid stable in water over 14 months |
| L1-40-09 | —OEt | 100 ml | 59.15 g | | 7.5 Hr 230° F. | 2 layers—lower layer water soluble clear liquid at 1% to 20% dilution in water—upper layer clear liquid slightly hydrophilic |
| 216-71-4 | —OMe | 5 ml | | 0.1 g | 17.5 Hr 215° F. | Clear to cloudy vicious liquid—NMR demonstrated strong reaction |

The reaction of the polydialkoxysiloxanes was demonstrated with several aliphatic alcohols (see Table I) but is believed also possible with aromatic alcohols. The reaction proceeds without a catalyst by coupling at elevated temperatures, e.g., 250° F. for up to 20 hr resulting in an ether bond between the silicone and the alcohol. When the alkoxy is methoxy or ethoxy the displaced alcohol must be removed or escape; for example, by bubbling an inert gas through the reaction. The product characteristics are determined by the alcohol used for the exchange and by the extent of replacement of the alkoxy groups. The starting siloxanes are insoluble but selection of glycerol as the alcohol results in a water soluble product. The reaction typically results in a heterogeneous mixture of products having chain lengths reflective of the number of polymer units in the starting material, which is usually 2-15. When run under the conditions exemplified below, there is substitution along the backbone of the silicone and little cross linking with the silicone. The products of the reaction can be separated by size exclusion chromatography or fractional distillation under reduced pressure.

The invention illustrates not only the chemical modification of linear polyalkoxy substituted siloxanes by reaction with alcohols but also the products and several therapeutic applications. The reaction is a transetherification in which an alkoxy group attached to the backbone of a linear polysiloxane is replaced with an alcohol. The reaction can be conducted with a wide selection of alcohols which can be selected to produce polysiloxanes with new properties. The chemical structures can be customized for specific applications, such as by reacting with alcohols selected for hydrophilicity or antibiotic activity. In particular, the invention demonstrates that "hydrophilic silicones," i.e., polysiloxanes substituted with hydrophilic groups, are useful as therapeutic treatments for skin irritations. Unexpectedly, hydrophilic glycerol polysiloxanes topically applied show remarkable healing in patients suffering from burns resulting from radiation therapy.

The structural similarity between the reactants and products of the transetherification reaction between polyalkoxysilanes and alcohols suggests that the changes in free energy are small. The position of equilibrium can be manipulated to increase product formation by removing the alcohol product formed from the transetherification. The reaction conditions as well as the efficiency of removal of the alkoxy group determine the amount and properties of substituted polysiloxane products which can be varied according to reaction conditions.

Hydrolysis of the transetherification products may occur either in storage or on the skin when used topically. This is more evident with polydimethoxysilane starting materials than with the diethoxy compound which exhibits only slight hydrolysis.

In accordance with the invention, reaction with 2-bromo-2-nitropropane-1,3-diol (sold commercially as BRONOPOL), which has primary alcoholic hydroxyl groups, produces a transetherification product with polydimethoxysilanes. The reaction is shown in Equation 3:

The use of the above reaction makes possible both the antibacterial action and the water solubility of BRONOPOL an integral part of the resulting silicone molecules.

Importantly, when polydimethoxysiloxane is employed as the starting material, complete removal of produced methanol is important when the product is used topically because of the influence of residual methanol on yield and the toxicity of methanol itself. The methoxy silicones therefore are not necessarily preferred as the starting materials for products that are intended for human use. Instead, if only ethoxy substituents are used, any hydrolysis produces only ethanol which has very low toxicity. While it is unlikely that appreciable hydrolysis occurs either in storage or on the skin, hydrolysis becomes much less important if only ethoxy groups are present in the starting material.

The mechanism of this reaction involves a nucleophilic attack on the silicon atom by the oxygen of a terminal hydroxyl group of an alcohol in order to form the —CH$_2$—O—Si— linkage. In the case of glycerol, this linkage appears to be protected to some extent against hydrolysis by the presence of the glycerol moiety.

The reaction is slow at room temperature; however, reaction rate is increased by heating to higher temperatures for longer periods of time. For example, heating glycerol with polydiethoxysiloxane for 5 hours at 225° C. (437° F.) will run the reaction nearly to completion while heating at lower temperatures requires much longer times, often up to 20 hours. When relatively volatile alcohols are substituted on the siloxane, the reaction can be driven to completion by removal of the alcohol, typically methanol or ethanol, as it forms during the reaction. This can be accomplished by bubbling air or nitrogen through the reaction mixture or by running the reaction in vacuuo.

When both glycerol and BRONOPOL are heated with a polydimethoxy or polydiethoxy siloxane, the use of the above reaction results in a composition having antibacterial action and water solubility as an integral part of the resulting silicone molecules.

EXAMPLES

The following examples are provided as illustrations of the invention and are in no way intended to be considered limiting.

Materials and Methods

Polydiethoxysiloxane and polydimethoxysiloxane (PS-9130-KG and PS-9120-KG) were purchased from UCT Specialties (Bristol, Pa.). Polydiethoxysiloxane (PS-9120-KG) and polydimethoxysiloxane (PS-9130-KG) were purchased from Gelest, Inc. (Morrisville, Pa. 19067).

Polydiethoxysiloxane purchased from UCT was a colorless to yellow liquid, soluble in water, specific gravity of 1.06 and boiling point of 160° C. (320° F.) at 760 mm Hg. The number of polymeric units averaged 2. Viscosity at 25° C. (77° F.) was 2.5-5.5 cS. Polydimethoxysiloxane was colorless to yellow liquid, water soluble, specific gravity of 1.2, boiling point 121° C. (250° F.) at 10 mm Hg, viscosity at 25° C. of 1-10cS and a refractive index of 1.38-1.40 at 25° C. (77° F.).

Example 1

Glycerol Reaction with Poly(diethoxy)siloxane 100 ml of polydiethoxysiloxane (Gelest, PS-9120-KG, polymeric units 2-8) was mixed with 50 g glycerol and heated for 5.5-7.5 hr at 130° F. under reduced pressure. Care was taken to exclude water from the reaction. Ethanol was removed from the reaction during the heating process. Two phases were present after heating and cooling to room temperature. The lower water soluble phase represented 46% of the volume while the water insoluble upper phase represented the remaining 54% of the volume.

The lower phase was a pale yellow to yellow stable liquid, specific gravity of 1.05-1.07. The product was 50-60% of the starting material and contained less than 5% tetraethoxysiloxane with the majority comprising modified poly(diethoxy) siloxanes having structure III:

where X and Y are —CH$_2$CHOHCH$_2$OH or —CH$_2$CH$_3$ but X and Y are not both —CH$_2$CH$_3$; and n is 2-15.

The hydroxyl groups on the glyceryl moiety render the polysiloxane hydrophilic or, in the extreme, water soluble, depending upon the number of glyceryl groups attached by the coupling reaction. Typically the water solubility is up to 5% with viscosities ranging from 3045 to 15320 cPs. Analysis by NMR and mass spec indicated that 30-50% of the ethoxy groups along the silicone backbone were replaced by glycerol.

The upper phase is a stable, clear, or slightly hazy, colorless, viscous liquid. It is insoluble and has a viscosity ranging from 5.25 to 5.82 cPs.

In another example, 50 ml of polydiethoxysiloxane purchased from Gelest (PSI-023) was heated with 250 ml propylene glycol for 20 hr at 250° F. and stirred once during heating. After cooling to room temperature, a solid separated from the reaction mixture. The solid weighed 121 g.

Example 2

BRONOPOL Reaction with Tetraethoxysilane

The reaction with BRONOPOL was conducted to show that the reaction conditions described in Example 1 would be suitable for exchanging an ethoxy group on a siloxane with a halogen substituted organic alcohol. BRONOPOL was selected because it has antibiotic properties and shows the feasibility of substituting a polyalkoxysiloxane with a compound that has properties potentially useful in combination with the properties of the siloxanes. With BRONOPOL, or other antimicrobial compounds, an antimicrobial barrier can be applied to skin or to other surfaces. This reaction can also be run with a polydialkoxysiloxane with varying numbers of polymeric units.

5 g of tetraethoxysilane and 1 g of BRONOPOL was heated at 215° F. for 5.5 hr, allowed to cool and the reaction container then sealed to prevent exposure to air. NMR showed that BRONOPOL reacted with the tetraethoxysilane. Mass spectrometry (MS) showed m/e of 346.45 corresponding to dimerization of tetraethoxysilane. MS also showed two products between BRONOPOL and tetraethoxysilane with molecular formulae of $C_{16}H_{34}Br_2N_2O_{13}Si_2$ and $C_{22}H_{48}Br_2N_2O_{16}Si_3$. Vacuum distillation of the product resulted in loss of the two bromine containing products observed in the crude product prior to distillation.

Half the product was heated at 60° C. (140° F.) under reduced pressure at 0.2 mm Hg to remove all volatile materials. NMR confirmed that BRONOPOL initially reacted with tetraethoxysiloxane.

Example 3

Surface Coating with Glycerol Substituted Polydiethoxysiloxane

The water soluble upper liquid phase of the product prepared in Example 1 was evaporated onto glass plates and tested for resistance to washing. The coated plates were compared to two commercially available silicones which were also coated on glass plates and washed with water or a detergent solution under the same conditions. Results showed that the new polysiloxane compositions had superior coating properties and were resistant to multiple washings. The glass surface is a model for skin. Comparative washing results are shown in Table 5.

TABLE 5

| Product | Source | Number of Washings |
|---|---|---|
| Liquid dimethacone | Dow corning | <10 |
| PEG silicone | Gelest, Inc. | <10 |
| Methoxy composition | One Unlimited, Inc. | >50 |
| Ethoxy Composition | One Unlimited, Inc. | >25 |

Example 4

Treatment of Skin Irritation

Figure 1:
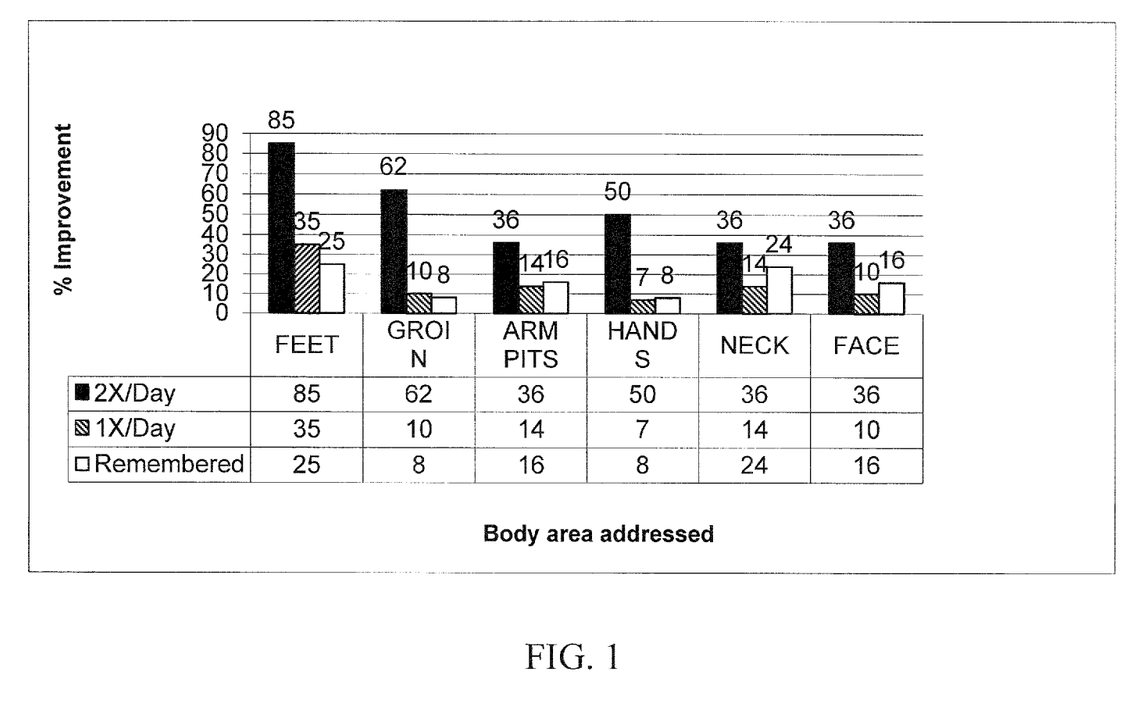

Tests of the lower phase water soluble composition prepared according to Example 1 were conducted on military personnel during a two week period of desert training. Volunteers were asked to topically apply the product as directed on areas where irritation or skin lesions were developing or had developed on their feet or other areas of the body during training. Data were collected from 50 men of whom 34 used the product substantially as directed while 14 rarely complied with directions for frequency of use. Results are summarized in FIG. 1 and in the tabulated data shown in Tables 6-8.

In the first group of 34 soldiers who responded to the questionnaire, stating that they did use the products:
  Group One: 8 used the products as instructed 2 times a day on at least one area.
  Group Two: 14 used the products only once a day.
  Group Three: 12 used the products when they remembered.

In Group One, 1 soldier admitted using the products only on his hands, 1 soldier saw no difference in the skin on his feet. 6 soldiers showed improvement on the skin of their feet, representing 75% of the group as a whole; or 85% of the soldiers that admitted using the products properly on their feet. In addition: 5 of the seven soldiers (55%) had improvement in the groin area; 4 of 8 (50%) showed improvement on their hands; 3 of 7 (42%) saw improvement in their armpit, neck and face areas. Only one man complained that his groin got slightly worse; 2 of 8 complained of mild irritation on their hands. Data are summarized in Table 6.

When the soldiers in Groups 2 and 3, who used the product only once daily and/or when they remembered were added, 5 of 14 in Group 2 also stated improvement in their feet while 3 of 12 in Group 3 also showed improvement in their feet. 14 of the 33 men who used the products on their feet (42%) were improved over the 2 week period. There was also an overall improvement in the neck area of 8 out of 33 soldiers (24%); improvement in the groin area of 21% as well as the arm pits and an 18% improvement in the face and hands. Of the men who responded, only 3 reported that their skin got worse. One of the 3 rarely used the product. The other 2 reported using it as recommended. In both cases, when they graded their skin the changes were only mildly worse. Data are summarized in Tables 7 and 8.

Results showed that: (1) while the sample is small, it seems to reflect a significant improvement in the group of men who had the most trouble with their skin; (2) the amount of improvement correlated directly with the number of times the products were used; (3) the foot area seemed to benefit most from the products, followed by the neck and then the groin area; and (4) the other areas (i.e. armpits, hands and face) also benefitted from routine use.

TABLE 6

| Group One—Twice A Day | | | |
|---|---|---|---|
| 8 total | Improved | Same | Worse |
| Feet | 6-75% | 1-13% | 0 |
| Groin | 5-62% | 2-25% | 1 |
| Arm Pits | 3-36% | 2-25% | 0 |
| Hands | 4-50% | 0 | 2 |
| Neck | 3-36% | 3-3% | 0 |
| Face | 3-36% | 4-50% | 0 |

TABLE 7

| Group Two—Once A Day | | | |
|---|---|---|---|
| 14 total | Improved | Same | Worse |
| Feet | 5-35% | 8 | 0 |
| Groin | 1-10% | 9 | 0 |
| Arm Pits | 2 | 9 | 0 |
| Hands | 1 | 10 | 0 |
| Neck | 2 | 9 | 0 |
| Face | 1-10% | 9 | 0 |

TABLE 8

| Group Three—When Remembered | | | |
|---|---|---|---|
| 12 total | Improved | Same | Worse |
| Feet | 3-25% | 8 | 1 |
| Groin | 1-10% | 9 | 1 |

TABLE 8-continued

Group Three—When Remembered

| 12 total | Improved | Same | Worse |
|---|---|---|---|
| Arm Pits | 2 | 7 | 1 |
| Hands | 1 | 10 | 1 |
| Neck | 3 | 8 | 1 |
| Face | 2 | 9 | 1 |

Example 5

Biofilm Inhibition

A 10 gallon glass fish tank was drained and dried. The inside glass of the tank was taped and three areas approximately 5 inches square were cut in the tape to expose the glass. Three different concentrations (1%, 5% and 10%) of the lower liquid phase of the material prepared in accordance with Example 1 as the glycerol substituted polyalkoxysiloxane were applied to the exposed areas and allowed to dry. The tank was filled with tap water and allowed to stand for 6 weeks at room temperature. Algae growth was significant on the inside of the tank except for all three of the taped areas.

Figure 2:
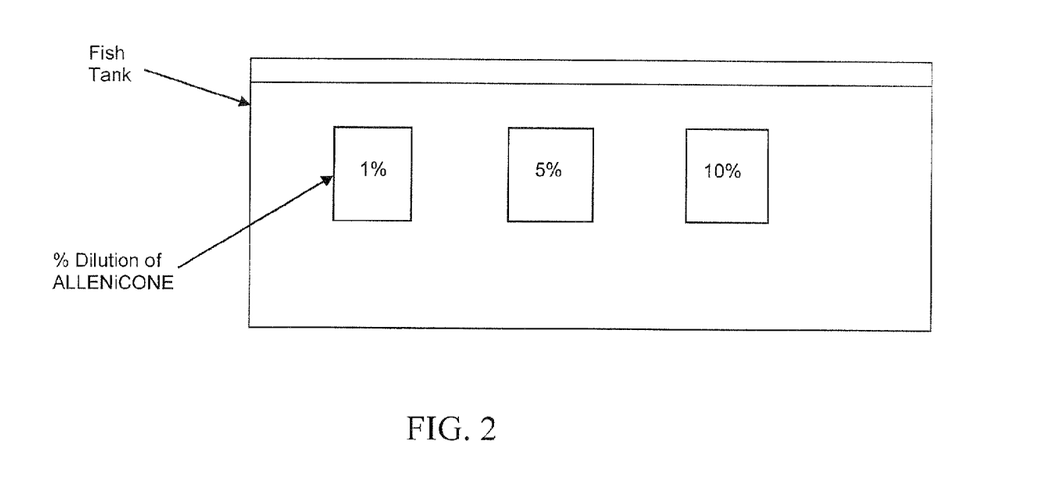
FIG. 2 is a photograph showing algae growth on the inside glass of a fish tank filled with water. The blank areas on the inside glass were surface coated with a polydiethoxysiloxane substituted with glycerol at 30-70% of the ethoxy positions. The algae growth was photographed after 2.5 months standing at room temperature.

Results are shown in FIG. 2. After 2.5 months, no algae were visible on the glass coated with the glycerol substituted diethoxypolysiloxane composition. Results indicate that the 1% solution was as effective in preventing biofilm formation as the higher concentrations at 5% and 10%.

In another application, a 0.25% aqueous solution of the glycerol substituted diethoxypolysiloxane was added to a fresh water fish tank containing several species of live fish and aquatic plants. The material coated the plants and the fish and fish gills without harm or visible effect. No algae growth was observed over a period of several months.

Example 6

Treatment of Chronically Draining Ear Post Surgery 35 patients were treated by inserting a packing saturated with a glycerol substituted linear diethoxysiloxane solution into the ear canal. The patients had undergone surgery for chronic ear disease and had developed a draining ear that failed to respond to conventional treatment consisting of a multistage process. Initial treatment is debridement of the ear. Four to six weeks of an antibiotic pack with, for example, CIPRO otic, CIPROdex, CORTISPORIN otic, Gentamicin Ophthalmic drops, followed until granulation was reduced. The patients were then instructed to dust the ear with boric acid powder 2-3 times per week and dry the ear with a hair dryer daily. If tolerated, this was followed by having the patient irrigate the ear with 3% hydrogen peroxide followed by a solution of either 70% isopropyl alcohol and vinegar or boric acid mixture and then dry the ear with a hair dryer.

The 35 patients underwent surgery for chronic ear disease and had developed a draining that failed to respond to the conventional treatment described above. Some had been under treatment for over two years. The ears were treated with a packing saturated with the glycerol substituted linear diethoxysiloxane and the packing changed every two weeks. Patients were instructed to apply drops of a 1% solution of the glyceryl polysiloxane twice daily to the packing.

Results showed that 28 of the patients fully healed and maintained a dry ear requiring minimal care. One patient discontinued treatment and continued to have a moist ear. Five patients had a significant reduction in drainage and granulation tissue. Two patients required skin grafting to obtain a dry ear.

Reduction in granulation was noted by four weeks with some epithelial formation usually observed. Initially thin and friable skin thickened over time to resemble normal skin except that epithelial skin was thin and more subject to trauma and breakdown. Once ear skin matured, little maintenance was required except for periodic cleaning and irrigation to prevent accumulation of squamous debris. Spontaneous healing of the chronic drainage was promoted and there was a reduction of need for revision surgery or secondary skin grafting.

Example 7

Topical Treatment of 200+ Irradiation Patients with Moist Dermatitis

A glycerol methoxysiloxane or glycerol ethoxysiloxane composition as described in example 1 was used in a spray application twice a day to areas of moist dermatitis and radiation burns. The series included patients undergoing radiation in the following areas: head and neck, chest was with axilla, perineal, and perirectal area with groin.

The composition was used after the failure of such products as silver sulfadiazine which was greasy and messy, and hydrocolloid dressings which did not adhere well to affected areas and were difficult to apply to the axilla and groin.

Patients typically reported pain relief within minutes and the moist wounds were noted within days to convert to dry wounds. These patients generally showed the above improvement during the first seven to ten days of product application.

The topical treatments were tolerated well by the entire group because of using a no touch delivery system and the immediate pain relief with enhanced wound healing. There was no instance of any allergic reaction noted in this patient population.

In addition to the above patient series, it was found that the topical glycerol methyoxylsiloxane spray has been the only product to alleviate the cutaneous side effects of chemotherapy, such as, that seen with TARCEVA which can cause a generalized skin rash and other agents which have been noted to cause a condition called "hand and foot syndrome" which can cause many cancer patients dry cracking skin on both their hands and feet which is painful and can lead to significant bleeding. In a matter of days both the bleeding and pain in these patients were alleviated, allowing this patient group to tolerate their full course of chemotherapy.

Example 8

Glycerol Methoxysiloxane Treatment of Cold Sores

Patients had between 1 and 3 sores, ranging in size between 0.2 and 0.5 cm. Areas treated topically included the buccal mucosa, palate, and mucosa of the lips. All areas involved were sprayed twice a day with either a 0.02% concentration of glycerol methoxysiloxane or 0.5% glycerol ethoxysiloxane. Treatment was started within 48 hrs of the start of cold sore symptoms and continued until fully healed which averaged 3-5 days from initiation of treatment.

What is claimed is:

1. A composition comprising one or more linear 2-15 unit siloxane polymers bonded to alkoxy groups wherein the alkoxy groups are selected from the group consisting of methoxy, ethoxy, propoxy, butoxy, pentoxy, hexoxy, 2-hydroxy-1- propoxy, 3-hydroxy-1-propoxy, 6-hydroxy-1-hexoxy, 3-hydroxy-2-bromo-2-nitro-1-propoxy, 2,3-dihydroxy-1-propoxy, 1,2-dihydroxy-3-propoxy and 1,3-dihydroxy-2-propoxy, provided that at least 30% of the silicon atoms are bonded to one or more alkoxys selected from the group consisting of 2-hydroxy-1-propoxy, 3-hydroxy-1-propoxy, 6-hydroxy-1-hexoxy, 3-hydroxy-2-bromo-2-nitro-1-propoxy, 2,3-dihydroxy-1-propoxy, 1,2-dihydroxy-3-propoxy and 1,3-dihydroxy-2-propoxy.

2. The composition of claim 1 wherein the siloxane polymers comprise ethoxy or methoxy groups.

3. The composition of claim 1 wherein about 30-70% of the alkoxy groups are 2,3-dihydroxy-1-propoxy, 1,2-dihydroxy-3-propoxy, or 1,3-dihydroxy-2-propoxy.

4. The composition of claim 1 wherein the alkoxy group is 3-hydroxy-2-bromo-2-nitro-1-propoxy, 2,3-dihydroxy-1-propoxy, 1,2-dihydroxy-3-propoxy or 1,3-dihydroxy-2-propoxy.

5. The composition of claim 1 wherein said one or more polymers has the structure:

where X is —CH$_2$CHOHCH$_2$OH and Y is —CH$_2$CHOHCH$_2$OH, —CH$_3$ or —CH$_2$CH$_3$ and n is 2-15.

6. The composition of claim 1 wherein said one or more polymers has the structure:

where X is —CH$_2$CH$_3$ or CH$_3$ and Y is —CH$_2$CHOHCH$_2$OH, propoxy, butoxy, pentoxy, hexoxy, 2-hydroxypropyl, 3-hydroxypropyl, or 6-hydroxyhexyl, and n is 2-8.

7. The composition of claim 1 which includes a pharmaceutically acceptable carrier.

8. A method for treatment or prevention of skin lesions in a mammal in need thereof, comprising administering to said mammal an effective amount of the composition of claim 1.

9. The method of claim 8 wherein the composition comprises a compound having the structure:

where X is —CH$_2$CHOHCH$_2$OH, and Y is —CH$_2$CH$_3$ or —CH$_3$ and n is 2-8 in a pharmaceutically acceptable formulation.

10. The method of claim 8 wherein the skin lesion is topical dermatitis, rosacea, acne, scarring, cold sore, skin rash, or mechanical or actinic skin damage.

11. The method of claim 8 wherein the skin lesion is a radiation burn.

12. A kit for treatment of skin lesions, comprising:
the composition of claim 1; and
an excipient or carrier suitable for mixing with said composition suitable to provide a topical formulation.

13. The kit of claim 12 wherein the composition includes a compound with the structure of claim 5 wherein n is 2-4.

14. The kit of claim 12 further comprising instructions for treating one or more skin lesions with said composition.

15. A method for inhibiting biofilm formation on a surface comprising, contacting a solid surface with a 0.25%-8% by volume solution of the composition of claim 1 to provide a coating resistant to biofilm formation.

16. The method of claim 15 wherein the solid surface is in contact with an aqueous medium.

17. The method of claim 15 wherein the solid surface is glass, ceramic, plastic, metal or polymer.

18. The method of claim 16 wherein the aqueous medium comprises a live fish or plant.

19. The method of claim 15 wherein the biofilm is algal or bacterial.

20. The method of claim 19 wherein the bacterial biofilm is produced by *Pseudomonas* or *Staphylococcus aureus*.

* * * * *

UNITED STATES PATENT AND TRADEMARK OFFICE
CERTIFICATE OF CORRECTION

PATENT NO. : 8,552,135 B2
APPLICATION NO. : 13/446064
DATED : October 8, 2013
INVENTOR(S) : Leonard William Luria It is certified that error appears in the above-identified patent and that said Letters Patent is hereby corrected as shown below:

In the Specification

Column 5,
Lines 21-22, "isopropylparaben, ispropylparaben and" should read
--isopropylparaben and--.

Column 8,
Lines 20-35, should read

Signed and Sealed this
Eleventh Day of March, 2014

Michelle K. Lee
*Deputy Director of the United States Patent and Trademark Office*